(12) United States Patent
Thys et al.

(10) Patent No.: US 10,918,781 B2
(45) Date of Patent: Feb. 16, 2021

(54) APPARATUS, SYSTEM AND METHOD FOR A PRESSURE-BASED DETECTION OF A CLOT

(71) Applicant: FRESENIUS MEDICAL CARE DEUTSCHLAND GMBH, Bad Homburg (DE)

(72) Inventors: Martin Thys, Grettstadt (DE); Joachim Noack, Bad Neustadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 152 days.

(21) Appl. No.: 15/770,330

(22) PCT Filed: Oct. 21, 2016

(86) PCT No.: PCT/EP2016/001762
§ 371 (c)(1),
(2) Date: Apr. 23, 2018

(87) PCT Pub. No.: WO2017/067668
PCT Pub. Date: Apr. 27, 2017

(65) Prior Publication Data
US 2018/0303999 A1 Oct. 25, 2018

(30) Foreign Application Priority Data
Oct. 21, 2015 (DE) .................... 10 2015 013 610.0

(51) Int. Cl.
*A61M 1/36* (2006.01)

(52) U.S. Cl.
CPC ........ *A61M 1/3639* (2013.01); *A61M 1/3672* (2013.01); *A61M 1/3627* (2013.01); *A61M 1/3653* (2013.01)

(58) Field of Classification Search
CPC .............. A61M 1/3627; A61M 1/3639; A61M 1/3653; A61M 1/3672; A61M 1/14; A61M 1/16; A61M 1/1601
See application file for complete search history.

(56) References Cited

FOREIGN PATENT DOCUMENTS

| DE | 2441210 | 3/1975 |
|---|---|---|
| DE | 69912899 | 8/2004 |
| DE | 10355042 | 6/2005 |
| DE | 102006032815 | 1/2008 |

(Continued)

*Primary Examiner* — Leslie R Deak
(74) *Attorney, Agent, or Firm* — Jacobson Holman, PLLC

(57) ABSTRACT

The present invention relates to an apparatus for a pressure-based detection of a clot in an extracorporeal blood circuit, wherein the apparatus comprises at least one cyclically operating pump for conveying the fluid located in the extracorporeal circuit and at least one pressure sensor which is arranged to determine the current pressure development over time in the fluid conveyed by the pump in a current conveying cycle of the pump, wherein the apparatus has at least one memory in which at least one reference pressure development is stored which is based on at least one pressure development over time which was determined in a conveying cycle of the pump preceding the current conveying cycle of the pump, and wherein the apparatus comprises at least one evaluation unit which is configured such that it compares the current pressure development with the reference pressure development over a corresponding time.

18 Claims, 3 Drawing Sheets

(56) References Cited

FOREIGN PATENT DOCUMENTS

Figure 1:
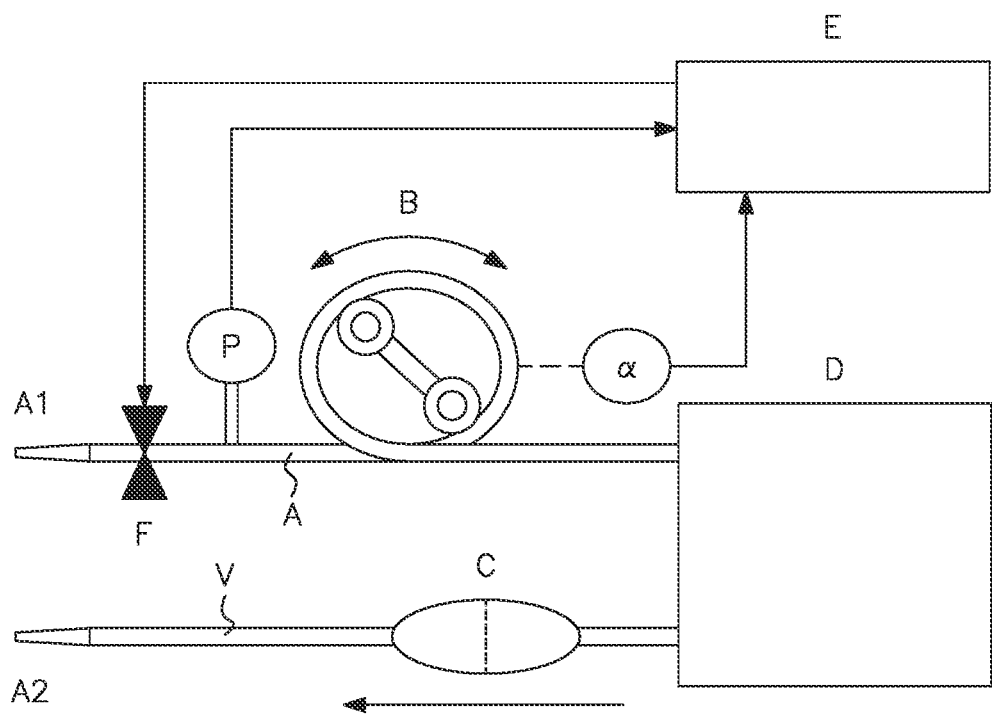

| DE | 102009018664 | 10/2010 |
|----|--------------|---------|
| DE | 102009024606 | 12/2010 |
| EP | 0981048 | 2/2000 |
| GB | 1480352 | 7/1977 |
| WO | WO 2014/149726 | 12/2010 |
| WO | WO 2013/000777 | 1/2013 |

APPARATUS, SYSTEM AND METHOD FOR A PRESSURE-BASED DETECTION OF A CLOT

The present invention relates to an apparatus for a pressure-based detection of a clot and to a system having at least one such apparatus, wherein the system comprises at least one blood treatment unit which has at least one extracorporeal circuit with which at least one cyclically operating pump cooperates for conveying the fluid located in the extracorporeal circuit.

The present invention furthermore relates to a method for a pressure-based detection of a clot.

It is known from the prior art that blood treatment apparatus such as hemofiltration units, hemodiafiltration units and hemodialysis units have a clot catcher in the extra-corporeal circuit which has the purpose of liberating blood from dangerously large clots by means of filtration prior to the infusion of the blood from the extracorporeal circuit into the patient.

The use of clot catchers admittedly brings along the advantage that the entry of such clots into the blood circuit of the patient is prevented, but it suffers from the disadvantage that the clot catcher in the flowing blood itself has negative effects on the blood. When the flowing blood impacts the clot catcher, turbulence arises. Due to this turbulence, physical and biochemical processes are initiated in the blood which can have the effect that the coagulation of the blood is activated or that blood cells are destroyed. On a coagulation of the blood, coagula can arise downstream of the clot catcher which can represent a danger for the patient in that they clog blood vessels or impede them being flowed through.

If a destruction of blood cells occurs (hemolysis), the blood can no longer sufficiently perform its function in vivo, which can likewise represent a dangerous situation for the patient.

Since the advantages of the clot catcher outweigh its disadvantages, they are usually used.

Within the framework of a conventional blood treatment, the blood is sucked into the extracorporeal circuit via the arterial line of the extracorporeal circuit, is treated therein, e.g. in a dialyzer, etc., and is pumped into the vein of the patient via the venous line. It is known in this case to provide a clot catcher in the venous line, i.e. in the line section of the extracorporeal circuit through which the blood is again supplied to the patient.

To supply the blood located in the extracorporeal circuit back to the patient after the blood treatment, a reinfusion of this blood takes place from the extracorporeal circuit to the patient. It is known in this respect that the blood still located in the extracorporeal circuit after the blood treatment is conveyed by means of displacement by a substitute fluid into the patient both through the arterial line and through the venous line of the extracorporeal circuit.

A flow reversal thus takes place in the arterial line with respect to the direction of blood flow during this reinfusion of the blood which follows the treatment and which is a lot shorter in time relative to the blood treatment. If a clot catcher were also installed in the arterial line, this would admittedly have the advantage within the framework of the rein-fusion that dangerously large clots would be prevented from reentering the patient's blood circulation. However, the clot catcher would have the above-described disadvantages during the comparatively long treatment time with respect to the creation of turbulence in the blood and thus with respect to any clot formation downstream of the clot catcher or with respect to any hemolysis. Against this background, no use is made of a clot catcher in the arterial line of the extracorporeal circuit.

WO 20131000777A1 discloses the measurement of pressure signals in an extracorporeal circuit. To determine a measured superposed pressure signal, pressure signals generated by the blood pump are filtered out of this pressure signal. A method is known from DE 24 41 210 A1 in which, in a cyclic manner, the venous line is blocked on the removal of the blood from the patient into the extracorporeal circuit and the arterial line is blocked on the supplying of the blood to the patient from the extracorporeal circuit and a conclusion is drawn on any irregularities from the length of the cycle.

It is the underlying object of the present invention to provide an apparatus, a system and a method in which the entry of clots into the patient within the framework of the reinfusion from the extracorporeal circuit can be detected.

This object is achieved by an apparatus having the features described below, by a system having the features described below, and by a method having the features described below.

Provision is accordingly made that the apparatus comprises at least one cyclically operating pump for conveying the fluid located in the extracorporeal circuit and at least one pressure sensor which is arranged to determine the current pressure development over time in the fluid conveyed by the pump in a current conveying cycle of the pump, wherein the apparatus has at least one memory in which at least one reference pressure development is stored which is based on at least one pressure development over time which was determined in a conveying cycle of the pump preceding the current conveying cycle of the pump, and wherein the apparatus comprises at least one evaluation unit which is configured such that it compares the current pressure development with the reference pressure development over a corresponding time.

A "cyclically operating pump" is to be understood as a pump whose conveying performance and/or whose pressure development in the conveyed fluid caused by the conveying performance is not constant in time, but rather preferably runs in work cycles consecutive in time. A pump is preferably understood by it which pumps in consecutive periods or cycles.

The apparatus furthermore has at least one memory in which at least one reference pressure development is stored which is based on an earlier pressure development over time. This earlier pressure development was determined by means of the pressure sensor in the fluid conveyed by the pump in at least one conveying cycle of the pump preceding the current pressure development.

Provision is preferably made that at least one measure is initiated by the evaluation unit when the current pressure development reaches or exceeds the reference pressure development.

A "comparison over a corresponding time" is to be understood such that corresponding points in time of the reference pressure development are compared with corresponding points in time of the current pressure development. The pressure is thus, for example, compared at the point in time t=10 seconds of the reference pressure development with the same point in time (t=10 seconds) of the current pressure development. If it is found in this process that the value of the current pressure development reaches or even exceeds the value of the reference pressure development, provision is preferably made that the evaluation unit initiates at least one measure, such as a stopping of the blood reinfusion, e.g. by the closing of a valve of the extracorporeal circuit, the stopping of the named pump or the like.

A clot of a danger-inducing size reduces the effective flow cross-section and can clog the patient connector or the needle connected thereto on the conveying to the patient from the extracorporeal circuit. The pressure increase which results is detected and as a preferred measure the conveying is stopped immediately to prevent the clot from entering into the patient's blood circulation. Since a clot is mechanically flexible, a clot which is only a little larger than the constriction located in front of it can under certain circumstances be pressed through the patient connector or through the needle connected thereto and optionally onward into the fistula in fractions of a second. The pressure monitoring in accordance with the invention is sufficiently sensitive to detect a pressure change caused by a clot and then to take corresponding measures.

Since the conveying behavior of a cyclically operating pump such as a hose roller pump is not even over time, the monitoring with respect to a fixed pressure limit is excluded due to too low a sensitivity at times.

The uneven volume flow of the medium to be conveyed (blood, substitute fluid or a mixture of the two) caused over time by the cyclically operating pump is repeated cyclically on each activation of an element involved in the conveying such as a hose roller which compresses the hose of the extracorporeal circuit over a part distance of its movement and thus effects the conveying of the fluid.

The apparatus in accordance with the invention or the system or the method are based on being able to compare the current pressure development in a currently running cycle in each case with a reference pressure development to be able to detect very quickly a pressure increase induced by a clot.

A partial region of a total pressure development which comprises a period or a partial period with periodically operating pumps is preferably compared with a reference pressure development.

The pump can, for example, be a peristaltic pump or a hose roller pump. However, other pumps which operate cyclically are also covered by the invention. All the pumps are covered by the invention which pulsate in the time development or which have a cyclic pressure development or which have a periodically fluctuating conveying rate, i.e. pumps which do not convey uniformly. A further example for such a pump is a membrane pump.

The reference pressure development is preferably based on a pressure development phase-shifted with respect to the current pressure development. It is thus conceivable, for example, to measure the pressure development during half a revolution of the pump and to use this as the reference pressure development, optionally with a supplement for the following half-revolution. If the pressure in the current conveying cycle is above the reference value development or the threshold value development or if it reaches it, one or more measures are preferably carried out such as the pump being stopped, a valve being closed and/or an alarm triggered.

The reference pressure development is preferably determined on the basis of the pressure development directly preceding the current pressure development. Only a comparatively small data storage effort is thus necessary.

The reference pressure development can generally be a pressure development from the past, i.e. a pressure development which preceded the current pressure development at any desired point in time. The reference pressure development is preferably a pressure development directly preceding the current pressure development such as the pressure development in a directly preceding period or partial period of the pump conveying or one or more of pressure developments or parts thereof which were determined in previous periods or partial periods, i.e. periods or partial periods disposed further back in time, of the pump conveying.

If a pump having two hose rollers is assumed which accordingly has two very largely identical conveying cycles per revolution, this would mean that the current pressure development always only has to be compared with the preceding pressure development which was determined during the preceding half-revolution of the pump.

The same naturally also applies accordingly to all other pumps which do not convey constantly such as cyclically operating pumps and not only to pumps which have two conveying cycles per complete revolution such as membrane pumps, for instance.

Provision is made in a further embodiment of the invention that the reference pressure development is formed by a pressure development determined in a preceding conveying cycle of the pump plus a supplement on this pressure development.

It is conceivable that an absolute supplement or a relative supplement is added to this measured pressure development. It is conceivable that the reference pressure development is formed in that the pressure development is raised by 5 to 50%. This supplement brings about the advantage that no false alarms are generated on small differences between conveying elements of the pump.

Provision is made in a further embodiment of the invention that the extracorporeal circuit has at least one arterial line and at least one venous line and that the pressure sensor is arranged in the arterial line and/or in the venous line.

The pressure sensor is preferably located in the arterial line. Preferably, no pressure sensor is arranged in the venous line. Instead, in a preferred embodiment, a clot catcher is arranged there which in turn is missing in the arterial line.

The invention can also be configured such that no clot catcher at all is arranged. It is generally also conceivable and covered by the invention to arrange a clot catcher both in the arterial line and in the venous line or only in one of these lines.

The invention can generally be used in the arterial line, in the venous line or both in the arterial line and in the venous line, i.e. the invention covers all of these embodiments.

In a further embodiment of the invention, the evaluation unit is configured such that, as a measure, it e.g. closes a valve in the extracorporeal circuit and/or stops the pump so that the clot is not conveyed onward and does not enter into the patient's blood circulation.

Alternatively or additionally, a signal can be output to a user such as an alarm signal, which signals the presence of a clot.

The present invention furthermore relates to a system having the features of described below. The system comprises at least one apparatus in accordance with the present invention and has at least one extracorporeal circuit which preferably has at least one connector by means of which the extracorporeal circuit can be connected to the patient. The at least one cyclically operating pump of the apparatus for conveying the fluid located in the extracorporeal circuit cooperates with the extracorporeal circuit.

The system can be formed by a blood treatment unit or can comprise it. In the first case, the components of the system are elements of the blood treatment unit; in the second case, at least one component of the system is not an element of the blood treatment unit, but is rather formed by an external unit.

The blood treatment unit can, for example, be a hemofiltration unit, a hemodialysis unit, a hemodiafiltration unit, an apheresis unit or an apparatus for medicating the patient.

The present invention furthermore relates to a hose set which is suitable and intended for use in an apparatus in accordance with the instant invention or for use in a system in accordance with the instant invention.

The hose set forms the extracorporeal circuit or a section thereof, wherein the hose set is provided with at least one connector for connecting the extracorporeal circuit to a patient and wherein the hose set has an arterial line and a venous line and wherein no clot catcher is arranged in the arterial line or no clot catcher is arranged in the venous line or no clot catcher is arranged in either line. The hose set can thus be formed without a clot catcher.

The present invention furthermore relates to a method having the features described below.

In accordance with the method in accordance with the invention provision is made that the current pressure development in the fluid conveyed by the pump is determined over time in a, current conveying cycle of the pump. This current pressure development is compared with the named reference pressure development. As stated above, at least one measure is initiated when the current pressure development exceeds or reaches the reference pressure development.

Provision is preferably made in this respect that the pump, which is preferably located in the arterial part of the extracorporeal circuit, runs in the opposite direction to the usual conveying direction during the blood treatment for carrying out this method. The fluid in the arterial line is thus not conveyed away from the connector, but toward the connector.

As stated above, the pressure measurement takes place in the arterial line and/or in the venous line. It is preferred if the pressure measurement takes place in the line in which no clot catcher is arranged.

The named measure can be the blocking of the extracorporeal circuit by one or more valves, the stopping of the pump, the outputting of a signal to the user such as an alarm or a plurality of these measures.

Provision is preferably made that the fluid, i.e. the blood, the mixture of fluid and substitute fluid or the substitute fluid itself which is conveyed from the extracorporeal circuit is not conducted through a clot catcher on the arterial side.

The reference pressure development can be based on a pressure run phase-shifted with respect to the current pressure development. It can be formed by a pressure development determined in the preceding conveying cycle of the pump plus a supplement on this pressure development.

In a preferred embodiment of the invention, the present invention thus relates to a system or to a method for the reinfusion of blood from an extracorporeal blood circuit back into the patient without a clot catcher having to be used. It is ensured by the pressure monitoring that if an elevated pressure value occurs due to a larger clot, counter-measures are initiated such as a pump stop or the closing of a valve, which is also to be understood as the closing of a hose clamp.

In a preferred embodiment of the invention, the pressure development which is modulated due to the hose pump in the extracorporeal blood circuit and which is phase-shifted by half a revolution is used as a reference pressure development or as a limit value curve for the pressure monitoring in accordance with the invention.

Further details and advantages of the invention will be explained in more detail with reference to an embodiment described in the drawing.

Figure 2:
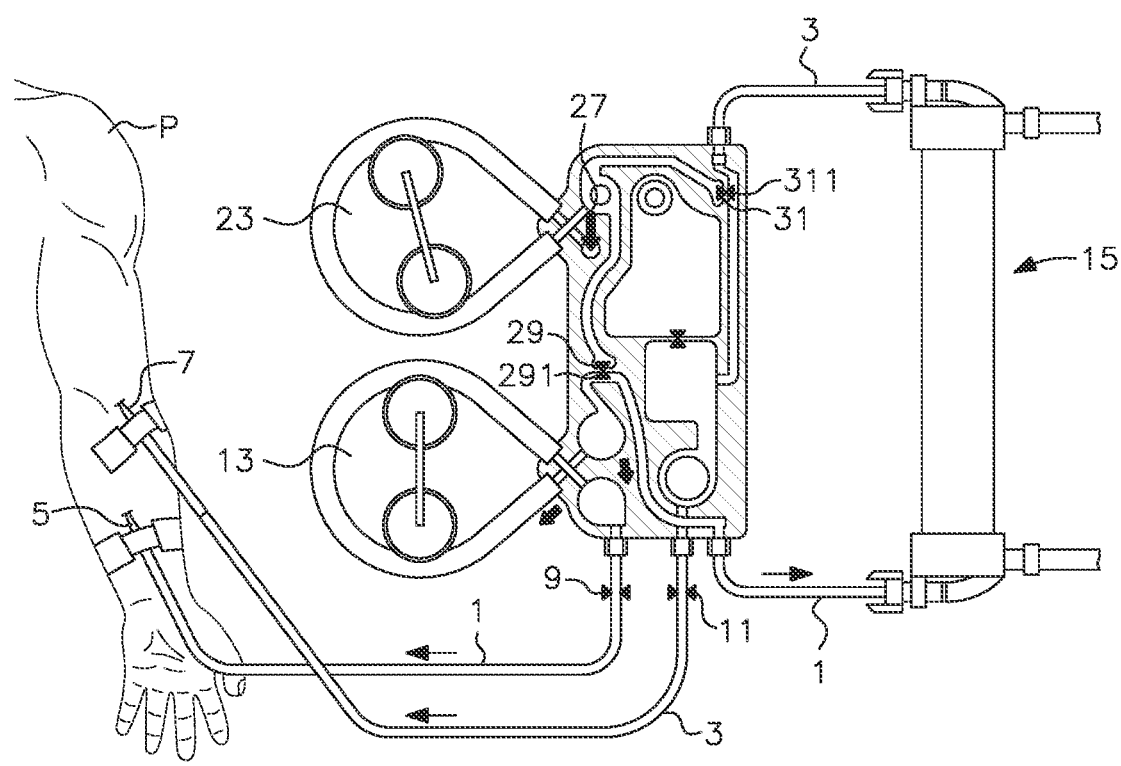
Figure 3:
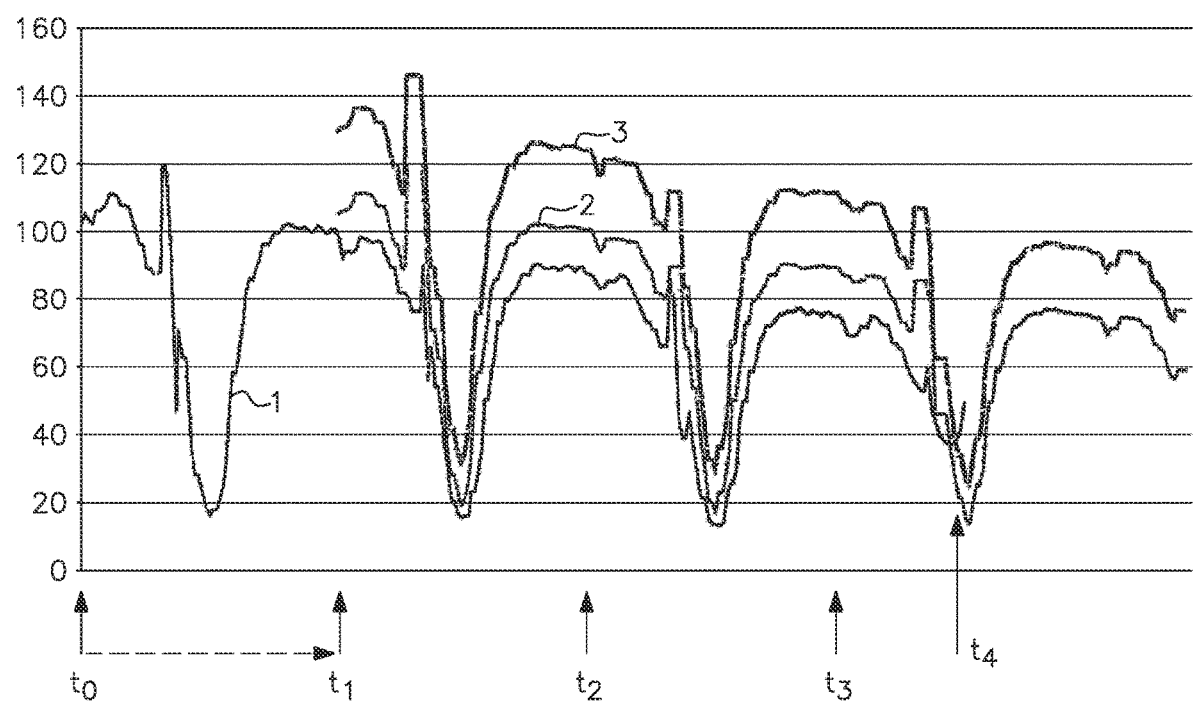

There are shown:

FIG. 1: a very simplified schematic view of a blood treatment unit with an extracorporeal blood circuit;

FIG. 2: a further view of a blood treatment unit with an extracorporeal blood circuit; and FIG. 3: a view of the pressure development over time for a plurality of conveying cycles.

Figure shows by the reference symbol A1 the arterial patient connection of an extra-corporeal blood circuit through which blood enters into the arterial line A by means of the pump B during the blood treatment. The blood is pumped through this arterial patient connection during the treatment by means of the pump B in the direction of the treatment apparatus D which can be a dialyzer. The treatment apparatus can provide substitution fluid. After the treatment, the blood moves in accordance with the direction of the arrow through the clot catcher C via the venous line V to the venous patient connection A2.

Reference symbol F denotes an electrically actuated clamp by means of which the arterial line A is blockable.

Reference numeral P denotes a pressure sensor which is located between this clamp F and the blood pump B.

An evaluation unit is marked by the reference symbol E which determines from the output signals of the pressure sensor and of an angle of rotation sensor which delivers the output signal a whether a pressure increase is present which could be caused by a clot; in this case it immediately closes the clamp F.

During the reinfusion of blood from the extracorporeal blood circuit which is subsequent to the blood treatment, blood is conveyed back into the patient from the treatment apparatus via the patent connections A1 and A2.

For this purpose, the pump B is operated in a direction (here: clockwise) opposite to the normal direction. This has the result that blood or the substitute fluid is not conveyed as during the treatment from the connection A1 to the pump B, but conversely from the pump B to the connection A1. The blood in the venous line V is likewise conducted back to the patient, and indeed via the connection A2, by means of displacement by a substitution fluid. There is thus no change of the direction of flow at the venous side in comparison with the direction of flow during the blood treatment.

As can be seen from FIG. 1, the clot catcher C is located only in the venous line V. The supply of a clot to the patient through the connection A2 is thus improbable at this side of the extracorporeal circuit. Such a clot catcher is not located at the arterial side, as can be seen from FIG. 1. To ensure that entry of a clot into the patient's blood circulation also does not take place at the arterial side, the method in accordance with the invention is carried out at the arterial side.

The present invention is, however, not restricted to the use of the method in accordance with the invention in the arterial side. Alternatively or additionally, the invention can also be used in the venous side of the extracorporeal blood circuit.

The embodiment in accordance with FIG. 1 describes a conceivable, but very simplified apparatus and mode of operation for the reinfusion.

A detailed description of a possible reinfusion can be found in DE 10 2009 024 606 A1, to which reference is herewith made in full. FIG. 2 shows an embodiment of DE 10 2009 024 606 A1 with reference to which an example for the reinfusion can be described as follows:

Reference numerals 5, 7 denote the arterial (5) and the venous (7) port to the patient. Reference numeral 1 denotes the arterial line and reference numeral 3 the venous line. A dialyzer or another blood treatment unit is denoted by reference numeral 15.

The arterial line 1 is blockable by the hose clamp 9 and the venous line 3 is blockable by the hose clamp 11.

To conduct the blood back into the patient from the extracorporeal blood circuit after the end of the blood treatment, the clamps 9, 11 are opened and the blood pump 13 and the substituate pump 23 are operated. The blood pump 13 rotates clockwise in accordance with FIG. 2 and thus against its conveying direction in which it conveys during the blood treatment and the substituate pump 23 rotates counter-clockwise and thus in its conveying direction in which it also conveys during the blood treatment. Substitution solution is introduced via the line 27. For this purpose, the predilution addition valve 291 of the predilution addition port 29 is. Alternatively or additionally, an addition at a postdilution addition port 31 is also conceivable. The postdilution addition valve 311 is closed in the embodiment shown here.

Due to the operation of the blood pump 13 against its conveying direction which it has during the blood treatment, the blood pump 13 pumps the blood back into the patient during the reinfusion, the blood being located in the section 1 of the extracorporeal circuit between the blood pump and the port 5. The substituate pump 23 conveys substitution fluid through the remaining part of the extracorporeal blood circuit, including the dialyzer 15, and in so doing displaces the blood located in this part. It moves back to the patient via the venous port.

FIG. 3 shows a pressure development with a pressure increase which is measured by the sensor, P at the point in time $t_0$ and which is caused by a clot.

The time periods $t_0$-$t_1$, $t_1$-$t_2$, $t_2$-$t_3$ etc. each describe the activity period of a conveying element, i.e. a respective conveying cycle, i.e. a conveying period, of the pump B. As can be seen from FIG. 3, the development of the pressure is a decreasing one overall since the mixture of blood and substitute fluid has a blood content which decreases in the course of the reinfusion, with the viscosity of the fluid falling and with a falling pressure being adopted in the system hose with an unchanging conveying performance of the pump.

The method in accordance with the invention starts at the start of the reinfusion, i.e. at the point in time $t_0$. The pump B conveys from the treatment apparatus D to the patient connection A1. In this respect, a typical pressure arises in the arterial line A which is continuously recorded in the evaluation unit E.

At the point in time $t_1$, a complete conveying cycle or activity cycle of an individual conveying element was recorded.

The evaluation unit E detects the end of a conveying cycle using the data of the angle of rotation sensor a of the pump B which is mechanically connected to the pump B or which forms an element of the pump B. Alternatively, a detection of the end of a conveying cycle by a detection of the pressure development or by calculation by means of pump speed and the time or the angle of rotation of the rotor and the gear ratio of the gearbox is conceivable and is covered by the invention.

The pressure value recorded in the first conveying cycle, optionally plus a supplement, is defined as an alarm threshold for the next following conveying cycle in the time period $t_1$-$t_2$.

In FIG. 1, the measured arterial pressure is denoted by the reference numeral 1, the arterial pressure in the respective preceding roller passage or conveying cycle is denoted by the reference numeral 2 and the threshold value or the alarm threshold is denoted by the reference numeral 3. Reference numeral 3 thus denote the reference pressure development with which the current pressure development 1 is compared.

An alarm threshold 3 is thus now present for the interval $t_1$-$t_2$ which is respectively compared with the current pressure 1 in this time interval. The respective current pressure 1, which is typically in the range from 0-150 mmHG, is compared with the alarm threshold 3 which typically lies in the range from 0-225 mmHg.

If the current pressure 1 exceeds the alarm threshold, i.e. the reference pressure development 3, the conveying of the fluid in the arterial line A is stopped immediately by closing the clamp F.

The alarm threshold 3 is calculated by the evaluation unit E such that the pressure is used at the same time within the activity cycle of the preceding conveying element or conveying cycle and is optionally additionally displaced by a factor toward the higher pressure (offset). This factor can be in the range from 5% to 50%. This makes it possible that differences between the two conveying elements do not generate any false alarms.

A negative offset is generally also possible and covered by the invention to adapt the threshold value accordingly on a large drop of pressure between the individual cycles.

The alarm threshold 3 for the interval $t_1$-$t_2$ is thus calculated from the pressure development of the preceding interval $t_0$-$t_1$ plus a supplement with respect to the embodiment in FIG. 3.

As can furthermore be seen from FIG. 3, the curves 2 and 3 for the time interval $t_0$-$t_1$ start offset in time. In order also to be able to define a reference value for this starting range $t_0$-$t_1$, the reference value is set in an embodiment of the invention to a fixed value or value development to an experience value from earlier measurements.

The embodiment relates to a hose roller pump having two conveying elements, i.e. having two rollers which are arranged opposite relative to the axis of rotation. The invention is generally not limited to this, but rather covers every cyclically operating pump such as also a peristaltic pump having more than two conveying elements.

The pressure measurement can be carried out in any patient line of the extracorporeal circuit, for example also after the clot filter in the venous line in order to recognize clots which have grown there.

However, the arrangement shown in FIG. 1 with the pressure detection and the clamp in the arterial line is particularly advantageous.

As stated above, some few mmHG are added to the pressure curve from the preceding roller passage or roller cycle in order to fix the actual alarm threshold, i.e. the reference pressure development.

If the measured pressure value 1 is at or above the reference pressure value 3, possible measures which can be considered are e.g. the closing of the clamp F, the stopping of the pump B, the continuation of the reinfusion by means of a method in which a container with substitute fluid is connected to connection A1 and said substitute fluid is subsequently conveyed by the pump B (forward) in the direction of the treatment device, such as the continuation of the reinfusion of only NaCl and the prevention of the backward conveying of the pump B or a combination of these measures.

The invention claimed is:

1. An apparatus for a pressure-based detection of a clot in an extracorporeal blood circuit, wherein the apparatus comprises at least one cyclically operating pump for conveying the fluid located in the extracorporeal circuit and at least one pressure sensor which is arranged to determine the current pressure development over time in the fluid conveyed by the pump in a current conveying cycle of the pump, wherein the apparatus has at least one memory in which at least one reference pressure development is stored which is based on at least one pressure development over time which was determined in a conveying cycle of the pump preceding the current conveying cycle of the pump, wherein the apparatus comprises at least one sensor for detecting the position of the conveying member or members of the pump, with the sensor being connected to the evaluation unit for a comparison corresponding in time between the current pressure development and the reference pressure development, and wherein the apparatus comprises at least one evaluation unit which is configured such that it compares the current pressure development with the reference pressure development over a corresponding time.

2. An apparatus in accordance with claim 1, characterized in that the evaluation unit or another unit of the apparatus is configured such that it carries out at least one measure when the current pressure development reaches or exceeds the reference pressure development.

3. An apparatus in accordance with claim 2, characterized in that the evaluation unit or the other unit is configured such that as a measure it closes at least one valve located in the extracorporeal circuit and/or stops the pump and/or outputs a signal to the user of the system.

4. An apparatus in accordance with claim 1, characterized in that the pump is pump which has a periodically fluctuating conveying rate so that a cyclic pressure development results in the fluid conveyed by the pump, with provision preferably being made that the pump is a peristaltic pump or a membrane pump.

5. An apparatus in accordance with claim 1, characterized in that the reference pressure development is based on a pressure development phase-shifted with respect to the current pressure development; and/or in that the reference pressure development is based on the pressure development directly preceding the current pressure development and/or on a pressure development further in the past.

6. An apparatus in accordance with claim 1, characterized in that the reference pressure development is formed by a pressure development determined in a preceding conveying cycle of the pump, plus a supplement on this pressure development.

7. An apparatus in accordance with claim 1, characterized in that the extracorporeal circuit has at least one arterial line and at least one venous line; and in that the pressure sensor is arranged in the arterial line and/or in the venous line.

8. An apparatus in accordance with claim 7, characterized in that no clot catcher is arranged in the arterial line or in the venous line in which the pressure sensor is arranged; or in that a clot catcher is located in the arterial line and/or in the venous line.

9. A system comprising at least one blood treatment unit which has the extracorporeal circuit and comprising at least one apparatus for a pressure-based detection of a clot in accordance with claim 1.

10. A system in accordance with claim 9, characterized in that the extracorporeal circuit is provided with at least one connector for connecting the extracorporeal circuit to a patient.

11. A system in accordance with claim 9, characterized in that the blood treatment unit is a hemofiltration unit, a hemodialysis unit, a hemodiafiltration unit, an apheresis unit or an apparatus for medicating.

12. A hose set for use in an apparatus in accordance with claim 1 or for use in a system having at least one blood treatment unit which has the extracorporeal circuit and at least one apparatus for a pressure-based detection of a clot in accordance with claim 1, wherein the hose set forms the extracorporeal circuit or a section thereof, wherein the hose set is provided with at least one connector for connecting the extracorporeal circuit to a patient, and wherein the hose set has an arterial line and a venous line, and wherein no clot catcher is arranged in the arterial line or in the venous line or in either line.

13. A method for a pressure-based detection of a clot, wherein the method comprises the cyclic conveying of fluid from an extracorporeal circuit of a blood treatment unit carried out by at least one pump, wherein in a current conveying cycle of the pump the current pressure development is determined over time in the fluid conveyed by the pump, and wherein this current pressure development is compared with a reference pressure development over a corresponding time which is based on an earlier pressure development over time which was measured in at least one conveying cycle of the pump preceding the current pressure development, characterized in that the pump is operated in the opposite direction to the direction in which it runs during the blood treatment for carrying out the method.

14. A method in accordance with claim 13, characterized in that at least one measure is carried out when the current pressure development reaches or exceeds the reference pressure development.

15. A method in accordance with claim 14, characterized in that the measure is the blocking of the extracorporeal circuit and/or the stopping of the pump and/or the outputting of a signal to the user.

16. A method in accordance with claim 13, characterized in that the extracorporeal circuit has at least one arterial line and at least one venous line; and in that the pressure measurement takes place in the arterial line and/or in the venous line.

17. A method in accordance with claim 13, characterized in that the fluid which is conveyed out of the extracorporeal circuit and whose pressure development is measured is not conducted through a clot catcher.

18. A method in accordance with claim 13, characterized in that the reference pressure development is based on a pressure development phase-shifted with respect to the current pressure development; and/or in that the reference pressure development is formed by a pressure development determined in a preceding conveying cycle of the pump, plus a supplement on this pressure development.

* * * * *